US00PP10940P

United States Patent [19]

Schuurman

[11] Patent Number: Plant 10,940

[45] Date of Patent: Jun. 1, 1999

[54] FLORIBUNDA ROSE PLANT NAMED 'SUNTINK'

[75] Inventor: Frank Schuurman, Aukland, New Zealand

[73] Assignee: DeVor Nurseries, Inc., Watsonville, Calif.

[21] Appl. No.: 08/859,581

[22] Filed: May 20, 1997

[51] Int. Cl.[6] ..... A01H 5/00

[52] U.S. Cl. ..... Plt./148

[58] Field of Search ..... Plt./22, 26, 148, Plt./141

[56] References Cited

PUBLICATIONS

UPOV-ROM, Jan. 1998, Plant Variety Database, GTI Jouve Retrieval Software, Citations for 'Suntink'.

Cairns, ed., 1993, "Modern Roses 10", The American Rose Society, Shreveport, Louisiana, p. 167.

Haring, ed., 1986, "Modern Roses 9", The American Rose Society, Shreveport, Louisiana, pp. 91–92.

*Primary Examiner*—Howard J. Locker

*Attorney, Agent, or Firm*—Christie, Parker & Hale, LLP

[57] ABSTRACT

A floribunda rose variety producing soft pink flowers.

1 Drawing Sheet

BACKGROUND OF THE INVENTION

The present invention relates to a new and distinct floribunda rose variety which was originated by my crossing as seed parent the variety known as 'White Dream' and as pollen parent the variety known as 'Evelien (a.k.a. 'Interlien' U.S. Plant Pat. No. 7,368).' The varietal denomination of this new rose is 'Suntink.'

SUMMARY OF THE INVENTION

Among the novel characteristics possessed by the new variety which distinguish it from its parents and all other varieties of which I am aware are its attractive, soft pink flowers borne in clusters of many blooms on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison with Parents

The new variety differs from its parents in flower color. Whereas 'White Dream' is a white flowered patio rose and 'Evelien' produces beige colored flowers, the new variety produces soft pink flowers.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.

*Seed parent.*—'White Dream'.

*Pollen parent.*—'Evelien'.

Class: Floribunda.

The following is a detailed description of the new variety, from specimens grown under glass in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

1. FLOWER

Blooming habit: Continuous.

A. Bud:

(1) *Size.*—Small.

(2) *Form.*—Pointed.

(3) *Color.*—When sepals first divide, bud color is near 50C to 49D with darker pink coloration toward point of petal attachment.

(4) *Sepals.*—Foliaceous, about 2.5 to 3 cm long, sepals cover green bud, then divide and spread to horizontal. Color: Near 144A.

(5) *Peduncle.*—Length: About 4 cm to about 6 cm. Aspect: Smooth. Strength: Slender. Color: Near 144D.

(6) *Bracts.*—Usually 1, acute, elliptical, long, about 3.5 to 4.4 cm below calyx.

B. Bloom:

(1) *Size.*—Average size when fully expanded — about 6 cm to about 7 cm.

(2) *Borne.*—Clusters of about 20 to 32 blooms.

(3) *Form.*—Slightly cupped, imbricated, petals curl and ruffle at maturity.

(4) *Petalage.*—Number of petals under normal conditions — about 26 to 30.

(5) *Color (⅓–½ open).*—Outer petals — Top surface: Near 49D. Undersurface: Top: Near 56D center: Near 56B with near 58D surrounding base. Inner petals — Top surface: Near 50D. Undersurface: Top & center: Near 49C, with bottom by base near 58D. Base of petals — Near 1C. General tonality at a distance: Light pink.

(6) *Color (fully open).*—Outer petals — Top surface: Near 49D. Undersurface: Near 49D with slight tinges of near 58D at base. Inner petals — Top surface: Near 49D on top with near 49C in center. Undersurface: Near 49D. Base of petals: Near 155A. General tonality at a distance: Light pink.

(7) *Color change.*—Bloom fades very slightly. Color remains constant very well. Petal top surface: Near 49D. Petal undersurface: Near 49D. Base of petals: Near 155A. General tonality at a distance: Light pink.

C. Petals:

(1) *Texture.*—Thin, smooth.

(2) *Appearance.*—Inside matte and outside matte.

(3) *Form.*—Elliptic, with ruffled edges, some undulated margins.

(4) *Arrangement.*—Imbricated.

(5) *Petaloids.*—Few about 4 to 6.

(6) *Persistence.*—Petals drop off cleanly.

(7) *Fragrance.*—Fruity fragrance.

(8) *Lasting quality.*—Average, about 9 to 11 days on plant and about 6 to 8 days after cutting.

2. REPRODUCTIVE ORGANS

A. Stamens:

(1) *Arrangement.*—Regularly arranged around styles.

(2) *Stamens.*—Anthers: Color — near 22A. Filaments: Color — near 1C.

(3) *Pollen.*—Color — near 22A.

B. Pistils:

(1) *Styles.*—Bunched, even, about 0.03 cm above stigma.

(2) *Stigmas.*—Color — near 154D.

C. Characteristics of hips: Not observed.

3. PLANT

A. Form: Upright, compact, height about 55 to 65 cm and spread about 30 to 40 cm, at first season.

B. Growth: Vigorous.

C. Foliage: Compound 3 to 5 leaflets.

(1) *Size.*—Small.

(2) *Quantity.*—Abundant.

(3) *Color.*—New foliage — upper side near 146A with tinges of near 181A on margins; underside near 146B with tinges of near 181A; mature foliage — upper side near 146A, underside near 146B.

(4) *Shape.*—Oval with pointed tip.

(5) *Texture.*—Upper side leathery, semi-glossy; underside leathery, veiny.

(6) *Edge.*—Serrate.

(7) *Serration.*—Denticulate.

(8) *Leaf stem.*—Color — medium green.

(9) *Stipules.*—Adnate with enlarged upper part; margin is bearded.

(10) *Rachis.*—Very small prickles underneath.

(11) *Petioles.*—Top near 146A, underside near 144B.

(12) *Auricle.*—Short, bearded, curving outward slightly.

(13) *Resistance to disease.*—Very resistant to mildew, rust and blackspot.

D. Wood:

(1) *New wood.*—Color near 146B with tinges of near 181A on side exposed to sun, bark smooth.

(2) *Old wood.*—Color near 146B, bark smooth.

E. Flower stem: About 40 cm to about 51 cm from last cut.

F. Thorns: Ordinary on basals and laterals, thin, flat, straight, about 0.9 to 1.1 cm, near 181A with near 144B on tips; irregular; no prickles.

G. Winter hardiness: Winter hardy in Watsonville, Calif.

I claim:

1. A new and distinct floribunda rose plant of the variety substantially as shown and described.

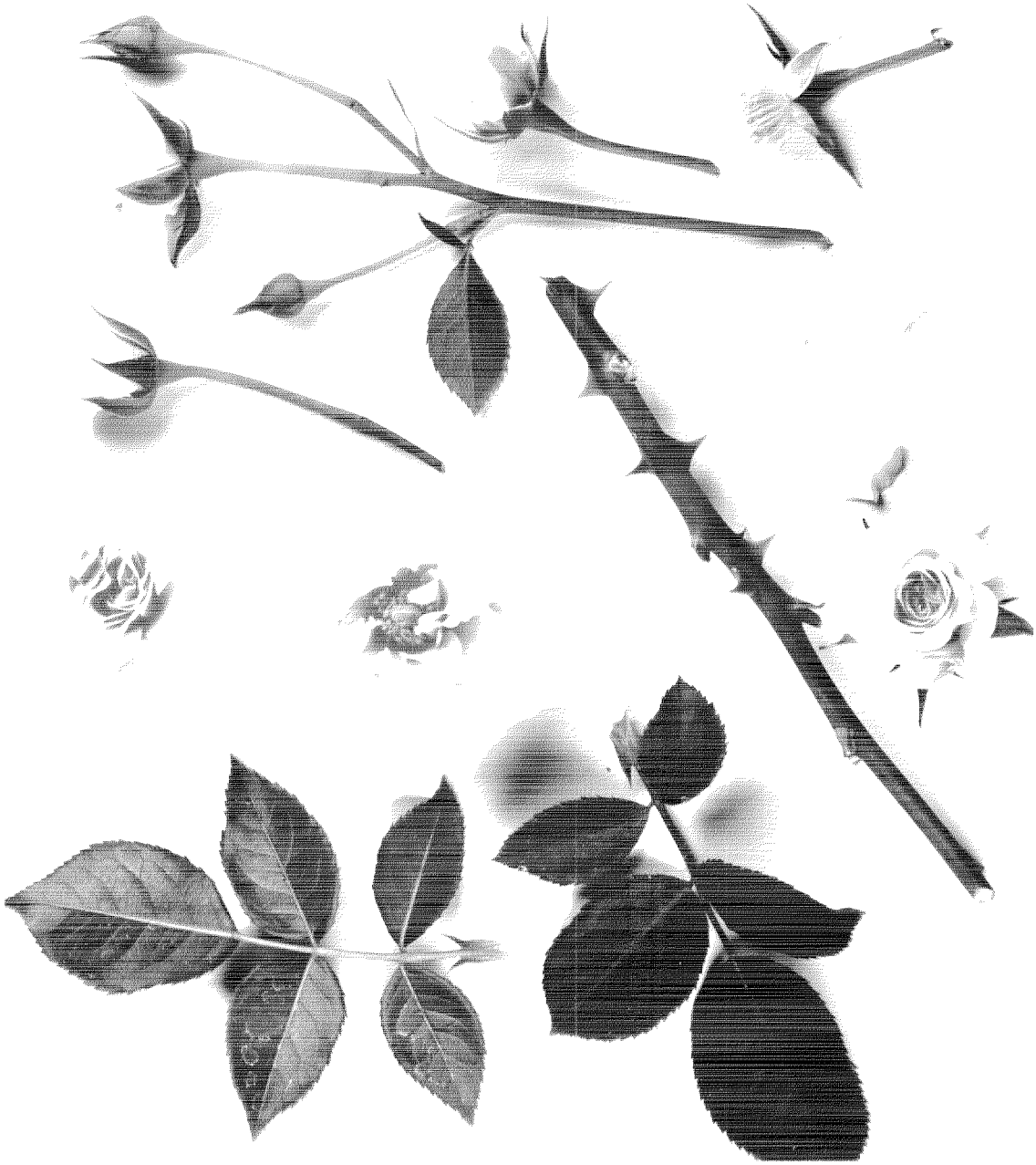

* * * * *